United States Patent [19]

Henry et al.

[11] Patent Number: 5,939,458
[45] Date of Patent: Aug. 17, 1999

[54] REDUCTION OF HAIR GROWTH

[76] Inventors: James P. Henry, 10257 Meadow Fence Ct., Myersville, Md. 21773; Gurpreet S. Ahluwalia, 8632 Stableview Ct., Gaithersburg, Md. 20882

[21] Appl. No.: 08/935,181

[22] Filed: Sep. 22, 1997

[51] Int. Cl.⁶ ................................................. A61K 31/195
[52] U.S. Cl. ...................... 514/567; 514/114; 514/212; 514/277; 514/297; 514/300; 514/365; 514/400; 514/419; 514/423; 514/424; 514/438; 514/478; 514/520; 514/557; 514/561; 514/562; 514/563; 514/575; 514/578; 514/588; 514/626; 514/641; 514/643; 514/653; 514/655; 514/663; 514/665; 514/666; 514/667; 514/673
[58] Field of Search ...................... 514/562, 557, 514/561, 563, 567, 575, 578, 588, 626, 641, 643, 653, 654, 655, 663, 665, 666, 667, 673, 114, 212, 277, 297, 300, 365, 400, 419, 423, 424, 425, 438, 478, 520

[56] References Cited

U.S. PATENT DOCUMENTS

| | | |
|---|---|---|
| 3,426,137 | 2/1969 | Philpitt et al. . |
| 4,039,669 | 8/1977 | Beylar et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Breuer et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Haverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,474,763 | 12/1995 | Shander et al. . |
| 5,554,608 | 9/1996 | Ahluwalia et al. . |
| 5,648,394 | 7/1997 | Boxall et al. . |
| 5,824,657 | 10/1998 | Hill et al. . |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 495 750 | 10/1970 | Sweden . |
| 1 458 349 | 12/1976 | United Kingdom . |
| WO 97/19672 | 6/1997 | WIPO . |
| WO 97/22329 | 6/1997 | WIPO . |

OTHER PUBLICATIONS

P. Schimmel, "Aminoacyl tRNA synthesases: general scheme of structure–function relationships in the polypeptides and recognition of transfer RNAs", Medline, AN=87297431, 1987 Abstract Only.

Andrew G. Messenger, "The Control of Hair Growth: An Overview", The Society for Investigative Dermatology, Inc., 1993.

Laske et al., "Investigations on the Antiproliferative Effects of Amino Acid Antagonists Targeting for Aminoacyl–tRNA Synthetases", Arch. Pharm (Weinheim) 32, 153–160, 1991.

Laske et al., "Investigations on the Antiproliferative Effects of Amino Acid Antagonists Targeting for Aminoacyl–tRNA Synthetases", Arch. Pharm (Weinheim) 322, 857–862, 1989.

Laske et al., "Investigations on the Antiproliferative Effects of Amino Acid Antagonists Targeting for Aminoacyl–tRNA Synthetases", Arch. Pharm (Weinheim) 322, 847–852, 1989.

Paul Schimmel, "Aminoacyl tRNA Synthetases: General Scheme of Structure–Function Relationships in the Polypeptides and Recognition of Transfer RNAs", Ann. Rev. Biochem., 56, 125–158, 1987.

Hampel et al., "Aminoacyl–tRNA Synthetases from Cultured CHO Cells", Methods in Enzymology, vol. LIX, 1979.

Kobori et al., "The Hair Cycle and its Control Mechanism", First International Symposium on Biology and Disease of the Hair, Tokyo, Japan, Oct. 6–9, 1975.

Loftfield et al., "Inhibitors of Amino Acid Activation", Metabolic Inhibitors A Comprehensive Treatise, vol. IV, 1973 pp. 107–109, 112–113, 116–117, 120–121, 124–125, 128–130.

Adachi et al., "Human Hair Follicles: Metabolism and Control Mechanisms", Journal of the Society of Cosmetic Chemists, 21, 901–924, Dec. 9, 1970.

CA126:157809, Ishigami et al, Dec. 24, 1996.

*Primary Examiner*—Rebecca Cook
*Attorney, Agent, or Firm*—Fish & Richardson P.C.

[57] ABSTRACT

Mammalian hair growth is reduced by applying an inhibitor of aminoacyl-tRNA synthetase to the skin.

65 Claims, No Drawings

REDUCTION OF HAIR GROWTH

The invention relates to reducing hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gammaglutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Aminoacyl-tRNA syntheses are a family of enzymes that are involved in cellular protein synthesis. In particular, the enzymes participate in the activation of amino acids and the subsequent linkage of the amino acids to corresponding tRNAs. There is at least one specific aminoacyl-tRNA synthetase and tRNA for each of the twenty natural amino acids that make up protein molecules. Aminoacyl-tRNA synthetases are discussed, for example, in P. Schimmel (1987) Ann. Rev. Biochem. 56: 125–158.

It has now been found that unwanted mammalian (including human) hair growth—particularly androgen-stimulated hair growth—can be reduced by applying to the skin a dermatogically acceptable composition including an inhibitor of an aminoacyl-tRNA synthetase in an amount effective to reduce hair growth. The unwanted hair growth which is reduced may be normal hair growth, or hair growth that results from an abnormal or diseased condition.

Examples of aminoacyl-tRNA synthetase inhibitors include S-trityl-L-cysteine; L-asparaginamide; 4-aza-DL-leucine; DL-serine hydroxamate; proflavine (hemisulfate salt); L-isoleucinol; N-phenylglycine; L-leucinol; L-methioninol; phe-leu-amide; tyramine; L-isoleucinol; 3,4-dehydro-DL-proline; S-carbamyl-L-cysteine; α-methyl-DL-methionine; chloro-L-alanine; cis-hydroxy proline; L-prolinol; L-histidonol; L-tyrprophan hydroxamate; DL-4-thiaisoleucine; DL-amino-ε-caprolactam; L-aspartic acid amide; DL-β-hydroxynorvaline; cis-4-fluoro-L-proline; trans-4-fluoro-L-carboxylic acid; α-methyl-DL-histidine; N-formyl-L-histidine; L-2-amino-3-sulfamoylpropionic acid; L-aspartic acid-β-hydroxamate; β-cyano-L-alanine; selenocystamine; 4-amino-n-butyric acid amide; DL-5-hydroxylysine; L-lysinhydroxamate; 3-(N-phenylacetyl) amino-2,6-piperidinedione (antineoplaston A10); 4-amino-4 phosphonobutyric acid; ethionamide; 1,2-diamino-3(4-imidazolyl) propane (histidinamine); α-methylhistidine; (S)-2-methylbutylamine; L-O-methylthreonine; DL-armentomycin (2-amino-4,4-dichlorobutyric acid); DL-3-dehydroarmentomycin; DL-3-hydroxyleucine; 5,5,5-trifluoro-DL-leucine; β-(3-aminocyclohexyl)-DL-alanine; DL-p-chloroamphetamine; trans-2,6-diaminohex-4-enoic acid; DL-2,6-diphthalimidocaproic acid methyl ester; DL-5-hydroxylysine; L-lysinhydroxamate; DL-4-oxalysine; DL-4-selenalysine; L-methioninamide; 2-amino-4-methylhex-4-enoic acid; (1S,2S)-2-amino-1-phenyl-1,3-propanediol; N-benzyl-D-amphetamine; N-benzyl-L-phenylalanine; N-benzyl-D-phenylethylamine; 1,3-bis (acetoxy)-2-nitro-1-phenylpropane (fenitropan); 1,2-diamino-3-(2,6-dichlorophenyl)propane; 1,2-diamino-3-hydroxy-5-phenylpentane; 1,2-diamino-3-phenylpropane; N-(2,6-dichlorobenzylidene)-2-phenylethylamine; N-(2,6-dichlorobenzyl)-2-phenylethylamine; N-(4-fluorobenzyl)-L-phenylalanine; DL-2-fluorophenylalanine; 2-hydroxyethyl-2-phenylammonium sulfate; α-and β-methyl-DL-phenylalanine; L-phenylalaninol; L-α-phenylglycine; DL-threo-β-phenylserine; β-2-thienyl-DL-alanine; N-trifluroacetyl-L-phenylalanine cyclohexyl ester; 2-aminomethyl-4-isopropyloxypyrrolidine oxalate; 2-amino-methylpyrrolidine; L-4-thiaproline; N-benzylethanolamine; N-(2,6-dichlorobenzyl) ethanolamine; N-(2,6-dichlorobenzylidene)ethanolamine; DL-β-hydroxyleucine; 1,2-diamino-5-phenyl-3-pentanol; DL-7-azatryptophan; DL-4-and DL-6-flurotryptophan; 5-hydroxytryptamine; L-5-hydroxytryptophan; DL-α-methyltryptamine; α- and β-methyl-DL-tryptophan; tryptamine; DL-2-amino-1-(4-hydroxyphenyl)-1-propanol; DL-3-fluorotyrosine; 3-iodo-L-tyrosine; 3-nitro-L-tyrosine; L-tyrosinol.HCl; L-threo-2-amino-3-chlorobutyric acid; hexafluoro-DL-valine; DL-norvaline; L-4-thialysine; DL-ethionine; N,N'-di-CBZ-L-lysine; DL-3-fluorophenylalanine; DL-4-fluorophenylalanine; and DL-3,4-dihydroxyphenylalanine. These compounds are known.

Many of the examples of aminoacyl-tRNA inhibitors are amino acid analogous and inhibit the specific aminoacyl-tRNA synthetase associated with the analogous amino acid, although a particular inhibitor may sometimes inhibit aminoacyl-tRNA synthetase associated with more than one amino acid. As used herein, "inhibitor of [name of amino acid] aminoacyl-tRNA synthetase" means a compound that inhibits at least the aminoacyl-tRNA associated with the amino acid. The amino acid may be one of the 20 naturally occurring amino acids (e.g., leucine, serine, etc.), or some other amino acid. As used herein, "aminoacyl-tRNA synthetase inhibitors" and a "inhibitor of aminoacyl-tRNA synthetase" means a compound that inhibits one or more aminoacyl-tRNA synthetase.

The aminoacyl-tRNA synthetase inhibitor preferably is incorporated in a topical composition that includes a non-toxic dermatologically acceptable vehicle or carrier which is adapted to be spread upon the skin. Examples of suitable vehicles are acetone, alcohols, or a cream, lotion, or gel which can effectively deliver the active compound. A vehicle is disclosed in U.S. Pat. No. 5,648,394. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

A composition may include more than one aminoacyl-tRNA synthetase inhibitor. For example, the composition may include two inhibitors of an aminoacyl-tRNA synthetase associated with a particular amino acid, or may include an inhibitor of an aminoacyl-tRNA synthetase associated with a first amino acid and an inhibitor of an aminoacyl-tRNA synthetase associated with a second amino acid. The composition optionally may also include other compounds that are known to reduce hair growth when applied topically.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. The duration of treatment to achieve a perceived reduction in hair growth may vary depending upon, for example, the severity and location of the unwanted hair growth. In humans, the composition, for example, may be applied once or twice a day, or even more frequently, for two weeks to six months (e.g., three months) to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an aminoacyl-tRNA synthetase inhibitor, the flank organs of each of a group of hamsters are shaved. To one organ of each animal 10 $\mu$l. of vehicle alone once a day is applied, while to the other organ of each animal an equal amount of vehicle containing a aminoacyl-tRNA inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 25%, more preferably at least about 50%, and most preferably at least about 60% when tested in the Golden Syrian hamster assay. A number of compositions containing an aminoacyl-tRNA synthetase inhibitor were tested in the Golden Syrian hamster assay; the results are provided in Table 1:

TABLE 1

| Inhibitor | Dose (%) | Vehicle | pH | Treated (mg) | Control (mg) | % Inhibition |
|---|---|---|---|---|---|---|
| S-trityl-L-cysteine | 7.5 | A | 6.5 | 0.35 ± .10 | 1.64 ± .14 | 80 ± .6 |
| L-asparaginamide | 10 | B | 5 | 1.00 ± .24 | 2.60 ± .42 | 66 ± 7 |
| 4-aza-DL-leucine.2HCL | 10 | B | 5.5 | 0.70 ± .08 | 2.02 ± .27 | 66 ± 3 |
| DL-$\alpha$-amino-$\epsilon$-caprolactam | 10 | D | 6.6 | 0.90 ± .16 | 2.30 ± .11 | 59 ± 9 |
| DL-serine hydroxamate | 10 | B | 7.5 | 1.28 ± .17 | 2.94 ± .34 | 56 ± 5 |
| proflavine hemisulfate | 10 | C | 5.5 | 1.41 ± .19 | 3.04 ± .24 | 52 ± 7 |
| L-isoleucinol | 10 | B | 7.5 | 1.20 ± .21 | 2.40 ± .38 | 51 ± 9 |
| N-phenylglycine | 10 | D | 3.0 | 1.37 ± .19 | 2.84 ± .22 | 51 ± 8 |
| L-leucinol | 10 | E | 8.0 | 1.55 ± .22 | 2.86 ± .34 | 46 ± 4 |
| L-prolinol | 10 | B | 7.5 | 1.31 ± .19 | 2.43 ± .26 | 45 ± 6 |
| L-histidonol | 10 | D | 7.4 | 1.88 ± .26 | 3.46 ± .18 | 45 ± 7 |
| L-methioninol | 10 | E | 7.5 | 1.55 ± .14 | 2.72 ± .27 | 42 ± 3 |
| phe-leu-amide | 10 | F | 4.5 | 1.18 ± .23 | 1.95 ± .19 | 41 ± 8 |
| tyramine | 10 | B | 5.0 | 1.20 ± .19 | 2.10 ± .13 | 41 ± 10 |
| 3,4-dehydro-DL-proline | 10 | B | 6.0 | 1.18 ± .18 | 2.00 ± .11 | 39 ± 9 |
| DL-$\beta$-hydroxynorvaline | 10 | B | 6.0 | 0.81 ± .15 | 1.40 ± .11 | 38 ± 13 |
| S-carbamyl-L-cysteine | 7.5 | G | 4.5 | 1.71 ± .17 | 2.55 ± .29 | 32 ± 6 |
| $\alpha$-methyl-DL-methionine | 15 | B | 6.5 | 1.10 ± .15 | 1.70 ± .40 | 31 ± 7 |
| L-aspartic acid amide | 10 | I | 6.9 | 1.38 ± .14 | 1.99 ± .21 | 30 ± 5 |
| chloro-L-alanine HCL | 10 | B | 4.5 | 2.39 ± .27 | 3.26 ± .26 | 25 ± 9 |
| cis-hydroxy-proline | 10 | B | 5.5 | 1.96 ± .18 | 2.60 ± .22 | 24 ± 7 |
| DL-4-thiaisoleucine | 10 | B | 5.0 | 2.36 ± .26 | 3.08 ± .16 | 23 ± 9 |
| lucinamide | 10 | B | 4.6 | 2.13 ± .28 | 2.77 ± .26 | 22 ± 10 |
| L-tyrprophan hydroxamate | 10 | H | 8 | 0.88 ± .10 | 1.10 ± .15 | 10 ± 17 |

Vehicles:
A--90% H$_2$O, 6% dipropylene glycol, and 4% ethanol.
B--68% water, 16% ethanol, 5% propylene glycol, 5% dipropylene glycol, 4% benzyl alcohol, and 2% propylene carbonate.
C--92% water, 3% propylene carbonate, and 5% benzyl alcohol.
D--80% ethanol, 17.5% water, 2% propylene glycol dipelargonate (Emerest 2388), and 0.5% propylene glycol.
E--50% dipropylene glycol and 50% ethanol.
F--60% ethanol, 25% dimethyl sulfoxide, 13.1% water, 1.5% propylene glycol dipelargonate (Emerest 2388), and 0.38% propylene glycol.
G--95.6% water and 4.4% dimethyl sulfoxide.
H--100% dimethyl sulfoxide.
I--84% water, 8% ethanol, 2.5% propylene glycol, 2.5% dipropylene glycol, 2% benzyl alcohol, and 1% propylene carbonate.

A dose response study with S-trityl-L-cysteine indicates that increasing the concentration of the inhibitor in the composition resulted in increased hair growth reduction. The results are shown in Table 2.

TABLE 2

Dose response inhibition of hair growth by S-trityl-L-cysteine

| Compound | Dose | pH | Treated (mg) | Control (mg) | % Inhibition |
|---|---|---|---|---|---|
| S-trityl-L-cysteine | 7.5% | 6.5 | 0.35 ± .10 | 1.64 ± .14 | 80 ± 6 |
| S-trityl-L-cysteine | 5% | 6.5 | 0.90 ± .17 | 1.95 ± .35 | 56 ± 6 |
| S-trityl-L-cysteine | 1% | 5.5 | 0.88 ± .10 | 1.10 ± .15 | 35 ± 9 |

Vehicle: 90% $H_2O$, 6% dipropylene glycol, and 4% ethanol

Inhibition of hair follicle aminoacyl-tRNA synthetase was determined using a modification of the procedure described by Hampel et. al (Aminoacyl-tRNA Synthetases from Cultured CHO Cells (1979) Methods in Enzymology, Vol. LIX, pp 229–234). A reaction mixture containing the following was used for each assay: 50 mM Tris (pH 7.4), 15 mM $MgCl_2$, 0.5 mM EDTA (adjusted to pH 7), 5 mM ATP (adjusted to pH 7, 0.35 mM CTP, 20 μM $^{14}$C amino acid and tRNA (50 μg/ml). Leucine and serine tRNA synthetase were assayed with a pH 8.6 buffer and a $MgCl_2$ concentration of 8 mM. The reaction mixture is mixed with the hair follicle extract so that the final assay volume is 100 μl. Typically, 90–95 μl of the reaction mixture was mixed with 5–10 μl of the hair follicles extract. The reaction was carried out at 37° C. for 60 minutes. The reaction was terminated by removing the reaction mixture and placing it on a piece of filter paper that had been soaked with 10% trichloroacetic acid. The filter paper was washed 3 times in 10% trichloroacetic acid and 3 times in 5% trichloroacetic acid. The filter paper was dried and the insoluble radioactivity, corresponding to the $^{14}$C-aminoacyl-tRNA, was counted in a scintillation counter.

The incorporation of the $^{14}$C amino acid varied from 178 dpm/mM to 3,093 dpm/mM in the assays of the amino acids mentioned above. Using this assay it was found that leucine incorporation into newly synthesized proteins was inhibited 18% by 0.96 μmole/ml leucinol and 83% by a similar concentration of leucinamide. In addition the incorporation of serine into newly synthesized proteins was inhibited 9% by DL-serine hydroxamate.

Other embodiments are within the claims.

We claim:

1. A method of reducing mammalian hair growth which comprises
    selecting an area of skin from which reduced hair growth is desired; and
    applying to said area of skin a dermatologically acceptable composition comprising an inhibitor of an aminoacyl-tRNA synthetase in an amount effective to reduce hair growth.

2. The method of claim 1, wherein said aminoacyl-tRNA synthetase is alanine aminoacyl-tRNA synthetase.

3. The method of claim 1, wherein said aminoacyl-tRNA synthetase is arginine aminoacyl-tRNA synthetase.

4. The method of claim 1, wherein said aminoacyl-tRNA synthetase is asparagine aminoacyl-tRNA synthetase.

5. The method of claim 1, wherein said aminoacyl-tRNA synthetase is aspartic acid aminoacyl-tRNA synthetase.

6. The method of claim 1, wherein said aminoacyl-tRNA synthetase is cysteine aminoacyl-tRNA synthetase.

7. The method of claim 1, wherein said aminoacyl-tRNA synthetase is glutamine aminoacyl-tRNA synthetase.

8. The method of claim 1, wherein said aminoacyl-tRNA synthetase is glutamic acid aminoacyl-tRNA synthetase.

9. The method of claim 1, wherein said aminoacyl-tRNA synthetase is glycine aminoacyl-tRNA synthetase.

10. The method of claim 1, wherein said aminoacyl-tRNA synthetase is histidine aminoacyl-tRNA synthetase.

11. The method of claim 1, wherein said aminoacyl-tRNA synthetase is isoleucine aminoacyl-tRNA synthetase.

12. The method of claim 1, wherein said aminoacyl-tRNA synthetase is leucine aminoacyl-tRNA synthetase.

13. The method of claim 1, wherein said aminoacyl-tRNA synthetase is lysine aminoacyl-tRNA synthetase.

14. The method of claim 1, wherein said aminoacyl-tRNA synthetase is methionine aminoacyl-tRNA synthetase.

15. The method of claim 1, wherein said aminoacyl-tRNA synthetase is phenylalanine aminoacyl-tRNA synthetase.

16. The method of claim 1, wherein said aminoacyl-tRNA synthetase is proline aminoacyl-tRNA synthetase.

17. The method of claim 1, wherein said aminoacyl-tRNA synthetase is serine aminoacyl-tRNA synthetase.

18. The method of claim 1, wherein said aminoacyl-tRNA synthetase is threonine aminoacyl-tRNA synthetase.

19. The method of claim 1, wherein said aminoacyl-tRNA synthetase is tryptophan aminoacyl-tRNA synthetase.

20. The method of claim 1, wherein said aminoacyl-tRNA synthetase is tyrosine aminoacyl-tRNA synthetase.

21. The method of claim 1, wherein said aminoacyl-tRNA synthetase is valine aminoacyl-tRNA synthetase.

22. The method of claim 1, wherein said inhibitor is S-trityl-L-cysteine.

23. The method of claim 1, wherein said inhibitor is L-asparaginamide.

24. The method of claim 1, wherein said inhibitor is 4-aza-DL-leucine.

25. The method of claim 1, wherein said inhibitor is DL-serine hydroxamate.

26. The method of claim 1, wherein said inhibitor is proflavine (hemisulfate salt).

27. The method of claim 1, wherein said inhibitor is L-isoleucinol.

28. The method of claim 1, wherein said inhibitor is N-phenylglycine.

29. The method of claim 1, wherein said inhibitor is L-leucinol.

30. The method of claim 1, wherein said inhibitor is L-methioninol.

31. The method of claim 1, wherein said inhibitor is phe-leu-amide.

32. The method of claim 1, wherein said inhibitor is tyramine.

33. The method of claim 1, wherein said inhibitor is 3,4-dehydro-DL-proline.

34. The method of claim 1, wherein said inhibitor is S-carbamyl-L-cysteine.

35. The method of claim 1, wherein said inhibitor is α-methyl-DL-methionine.

36. The method of claim 1, wherein said inhibitor is chloro-L-alanine.

37. The method of claim 1, wherein said inhibitor is cis-hydroxy proline.

38. The method of claim 1, wherein said inhibitor is L-prolinol.

39. The method of claim 1, wherein said inhibitor is L-histidonol.

40. The method of claim 1, wherein said inhibitor is L-tyrprophan hydroxamate.

41. The method of claim 1, wherein said inhibitor is thioisoleucine.

42. The method of claim 1, wherein said inhibitor is DL-amino-ε-caprolactam.

43. The method of claim 1, wherein said inhibitor is L-aspartic acid amide.

44. The method of claim 1, wherein said inhibitor is DL-β-hydroxynorvaline.

45. The method of claim 1, wherein said inhibitor is selected from the group consisting of cis-4-fluoro-L-proline; trans-4-fluoro-L-carboxylic acid; α-methyl-DL-histidine; N-formyl-L-histidine; L-2-amino-3-sulfamoylpropionic acid; L-aspartic acid-β-hydroxamate; β-cyano-L-alanine; selenocystamine; and 4-amino-n-butyric acid amide.

46. The method of claim 1, wherein said inhibitor is selected from the group consisting of DL-5-hydroxylysine; L-lysinhydroxamate; 3-(N-phenylacetyl)amino-2,6-piperidinedione; 4-amino-4 phosphonobutyric acid; ethionamide; 1,2-diamino-3(4-imidazolyl) propane; α-methylhisidine; (S)-2-methylbutylamine; L-O-methylthreonine; and (2-amino-4,4-dichlorobutyric acid).

47. The method of claim 1, wherein said inhibitor is selected from the group consisting of DL-3-dehydroarmentomycin; DL-3-hydroxyleucine; 5,5,5-trifluoro-DL-leucine; β-(3-aminocyclohexyl)-DL-alanine; DL-p-chloroamphetamine; trans-2,6-diaminohex-4-enoic acid; DL-2,6-diphthalimidocaproic acid methyl ester; DL-5-hydrqxylysine; L-lysinhydroxamate; and DL-4-oxalysine.

48. The method of claim 1, wherein said inhibitor is selected from the group consisting of DL-4-selenalysine; L-methioninamide; 2-amino-4-methylhex-4-enoic acid; (1S, 2S)-2-amino-1-phenyl-1,3-propanediol; N-benzyl-D-amphetamine; N-benzyl-L-phenylalanine; N-benzyl-D-phenylethylamine; 1,3-bis(acetoxy)-2-nitro-1-phenylpropane; and 1,2-diamino-3-(2,6-dichlorophenyl) propane.

49. The method of claim 1, wherein said inhibitor is selected from the group consisting of 1,2-diamino-3-hydroxy-5-phenylpentane; 1,2-diamino-3-phenylpropane; N-(2,6-dichlorobenzylidene)-2-phenylethylamine; N-(2,6-dichlorobenzyl)-2-phenylethylamine; N-(4-fluorobenzyl)-L-phenylalanine; DL-flurophenylalanine; 2-hydroxyethyl-2-phenylammonium sulfate; methyl-DL-phenylalanine; L-phenylalaninol; and L-α-phenylglycine.

50. The method of claim 1, wherein said inhibitor is selected from the group consisting-of DL-threo-β-phenylserine; β-2-thienyl-DL-alanine; N-trifluroacetyl-L-phenylalanine cyclohexyl ester; 2-aminomethyl-4-isopropyloxypyrrolidine oxalate; 2-aminomethylpyrrolidine; L-4-thiaproline; N-benzylethanolamine; N-(2,6-dichlorobenzyl)ethanolamine; N-(2,6-dichlorobenzylidene)ethanolamine; and DL-β-hydroxyleucine.

51. The method of claim 1, wherein said inhibitor is selected from the group consisting of 1,2-diamino-5-phenyl-3-pentanol; DL-7-azatryptophan; DL-flurotryptophan; 5-hydroxytryptamine; L-5-hydroxy-tryptophan; DL-α-methyltryptamine; methyl-DL-tryptophan; tryptamine; DL-2-amino-1-(4-hydroxyphenyl)-1-propanol; and DL-3-fluorotyrosine.

52. The method of claim 1, wherein said inhibitor is selected from the group consisting of 3-iodo-L-tyrosine; 3-nitro-L-tyrosine; L-tyrosinol.HCl; L-threo-2-amino-3-chlorobutyric acid; hexafluoro-DL-valine; DL-norvaline; L-4-thialysine; DL-ethionine; N,N'-di-carbsbenzoxy-L-lysine; DL-3-fluorophenylalanine; DL-4-fluorophenylalanine; and DL-3,4-dihydroxyphenylalanine.

53. The method of claim 1, wherein the concentration of said inhibitor of in said composition is between 0.1% and 30%.

54. The method of claim 1, wherein the composition provides a reduction in hair growth of at least 20% when tested in the Golden Syrian hamster assay.

55. The method of claim 1, wherein the composition provides a reduction in hair growth of at least 50% when tested in the Golden Syrian hamster assay.

56. The method of claim 1, wherein the composition provides a reduction in hair growth of at least 60% when tested in the Golden Syrian hamster assay.

57. The method of claim 1, wherein the inhibitor is applied to the skin in an amount of from 10 to 3000 micrograms of said inhibitor per square centimeter of skin.

58. The method of claim 1, wherein said mammal comprises a human.

59. The method of claim 58, wherein said area of skin is on the face of the human.

60. The method of claim 58, wherein said area of skin is on a leg of the human.

61. The method of claim 58, wherein said area of skin is on an arm of the human.

62. The method of claim 58, wherein said area of skin is in an armpit of the human.

63. The method of claim 58, wherein said area of skin in on the torso of the human.

64. The method of claim 58, wherein said human is a woman suffering from hirsutism.

65. The method of claim 1, wherein said hair growth comprises androgen-stimulated hair growth.

* * * * *

UNITED STATES PATENT AND TRADEMARK OFFICE
CERTIFICATE OF CORRECTION

PATENT NO. : 5,939,458
DATED : August 17, 1999
INVENTOR(S) : James P. Henry and Gurpreet S. Ahluwalia It is certified that error appears in the above-identified patent and that said Letters Patent is hereby corrected as shown below:

<u>Title page,</u>
References Cited, under U.S. Patent Documents, in the citation
5,554,608   9/1996   Ahluwalia et al. .

Delete "9/1996" and insert -- 10/1996 --.

Signed and Sealed this

Twenty-eighth Day of August, 2001

Attest:

*Nicholas P. Godici*

NICHOLAS P. GODICI
*Attesting Officer*   *Acting Director of the United States Patent and Trademark Office*